United States Patent
Bristow et al.

(10) Patent No.: US 9,913,472 B2
(45) Date of Patent: Mar. 13, 2018

(54) AGROCHEMICAL FORMULATION, METHOD MAKING, AND METHOD OF USING

(71) Applicant: ROTMAN AGROCHEM INTERNATIONAL COMPANY LIMITED, Chai Wan (HK)

(72) Inventors: James TImothy Bristow, Hong Kong (CN); Yifan Wu, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 23 days.

(21) Appl. No.: 14/313,544

(22) Filed: Jun. 24, 2014

(65) Prior Publication Data

US 2015/0366205 A1    Dec. 24, 2015

(51) Int. Cl.
  *A01N 43/90*  (2006.01)
  *A01N 43/14*  (2006.01)
  *A01N 43/50*  (2006.01)
  *A01N 43/40*  (2006.01)

(52) U.S. Cl.
  CPC .............. *A01N 43/90* (2013.01); *A01N 43/14* (2013.01); *A01N 43/40* (2013.01); *A01N 43/50* (2013.01)

(58) Field of Classification Search
  CPC ............................................. A01N 1/00–65/48
  See application file for complete search history.

(56) References Cited

U.S. PATENT DOCUMENTS 5,773,422 A * 6/1998 Komer ................. A61K 9/0019
                                                                514/30
2003/0055089 A1 * 3/2003 Sirinyan ................ A01N 43/90
                                                                514/341
2006/0039944 A1 * 2/2006 Narayanan ............ A01N 25/30
                                                                424/408
2008/0255204 A1 * 10/2008 Davies ................... A01N 25/02
                                                                514/341
2010/0286217 A1 * 11/2010 Annis ..................... A01N 25/02
                                                                514/372
2012/0196821 A1 * 8/2012 Sargent ................. A01N 43/90
                                                                514/30

FOREIGN PATENT DOCUMENTS

CN          1500492        *  6/2004
CN       102369948 A          3/2012
WO    WO 2011/134817       * 11/2011

OTHER PUBLICATIONS

Machine translation of CN 1500492 (2004).*
Tisserat, B. et al "Stimulation of short-term plant growth . . . " HortSci. (2011) vol. 46, No. 12, pp. 1650-1654.*
International Search Report for PCT/CN2015/081020 dated Sep. 21, 2015.

* cited by examiner

*Primary Examiner* — Leigh C Maier
(74) *Attorney, Agent, or Firm* — Dickinson Wright PLLC

(57) ABSTRACT

Agrochemical formulations for treating plants, which formulations comprise, as cosolvent, polyethylene glycol (average molecular weights ranging from 200 to 400) or polypropylene glycol (average molecular weights ranging from 300 to 400) or mixtures, and, if appropriate, further additives, a process for preparing these formulations, their use for treating plants and/or their habitat and for increasing the efficacy and plant compatibility of these formulations, and for reducing volatile emission potential of these formulations.

10 Claims, No Drawings

AGROCHEMICAL FORMULATION, METHOD MAKING, AND METHOD OF USING

BACKGROUND

Field

Disclosed herein are agrochemical formulations for treating plants, processes for preparing these formulations and processes for their use for treating plants and/or their habitat.

Description of Related Art

Agrochemical active components (sometimes referred to as agrochemical active ingredients) are often solid particles, crystal-like particles or oily liquids, which do not disperse in water, or disperse only with difficulty, but which are to be brought into aqueous suspension for their final use. These agrochemical active ingredients, such as herbicides, pesticides, insecticides, and the like are sometimes first dissolved in a water immiscible solvent. Such an agrochemical active ingredient when dissolved in a water immiscible solvent is referred to as an Emulsifiable Concentrate (EC).

Optionally, surfactants are added before the solution is emulsified in water. The solution of the active ingredient in the water immiscible solvent is also used for the convenience of e.g. transportation, storage, and/or dosing with water.

Sometimes, some water is already added to the formulation, pre-forming an emulsion in water (EW). A special type of EW are so-called micro-emulsions (ME), where the droplets of water immiscible solvent with active components are so small that light is not scattered, providing a water-clear or translucent liquid.

These EC or EW formulations comprise, for example, emulsifiers and/or dispersants, solvents and, additionally the cosolvent such as VOCs. In general, the efficacy of these agrochemical active compound formulations is very good.

Solvents often used to provide EC or EW include aromatic hydrocarbons, such as SOLVESSO® solvents of Exxon Mobil, paraffinic hydrocarbons such as EXXSOL® solvents of Exxon Mobil, cyclic hydrocarbons such as cyclo-hexanone and isophorone, pyrrolidone solvents such as N-methylpyrrolidone (NMP) and ester solvents such as methyl-oleate and EXXATE® solvents of ExxonMobil. These solvents often have the disadvantages that they exhibit significant toxicity to the users exposed to them, they are highly volatile, and/or they have a flash point causing them to be considered highly flammable.

As a result, the United States Environmental Protection Agency reviews ingredients in pesticidal formulations in addition to the active ingredients present. In Europe, the E.E.C. Council is at an advanced stage of introducing legislation for regulating the use of volatile organic compounds (VOC) and will shortly require an eco-labelling of formulations which contain such VOCs. Further, Canada and Germany already have a system of labelling.

SUMMARY

In the context of research for novel agrochemical auxiliaries which improve the environmental properties of such formulations, we investigated alternatives to the above said VOC cosolvents. However, a criterion for substitution for the VOC cosolvent was that the substitution not affect the quality or performance of the resulting formulations. Thus, the amount of the active compound should remain as low as possible, and the action of the active compounds should not be reduced. At the same time, it was to be ensured that the formulations are easy to apply on the field, for example, by means of customary machinery.

It is also desirable to provide novel agrochemical EC or EW formulations which allow a considerably improved uptake of the formulated active compound or the formulated active compound combination via the leaves and, as a result, which show considerably improved biological action. As a result, in another embodiment, the present disclosure relates to crop treatment compositions comprising the agrochemical formulations disclosed herein.

The methods and formulations described herein provide a method for increasing the efficacy of an active compound or a combination of active compounds.

Also disclosed herein is a method for reducing the volatile emission potential of the active compound or combination of active compounds in a formulation.

In another embodiment is disclosed a method for treating plants or protecting plants against pests.

The formulation according to embodiments disclosed herein can comprise, in addition to any agrochemically active compound(s) in question, at least one emulsifier, optionally at least one dispersant, at least one solvent and, polyethylene glycol (average molecular weights ranging from 200 to 400) and/or polypropylene glycol (average molecular weights ranging from 300 to 400), or mixtures thereof. One or more agrochemically acceptable additives may also be present.

The concentration of the individual components in the formulation according to the invention can be varied within a relatively wide range.

Thus, the content of agrochemically active compound or combination of agrochemically active compounds is from 0.1% to 60% by weight, preferably from 5% to 50% by weight. The content of emulsifiers can be from 0.5% to 80% by weight, preferably from 0.5% to 60% by weight. The content of dispersant is generally from 0 to 10% by weight, preferably from 0.5% to 5% by weight. The content of solvent is generally from 5% to 80% by weight, preferably from 10% to 40% by weight. The content of polyethylene glycol (average molecular weights ranging from 200 to 400) and/or polypropylene glycol (average molecular weights ranging from 200 to 400), or mixtures thereof is generally from 10% to 90% by weight, preferably from 15% to 60% by weight. The sum of the individual components and possible further ingredients or additives of the formulation is always 100%.

The components of the formulation according to the invention are generally present in at least the following amount and forms (unless stated otherwise, all stated figures are in percent by weight, based upon the weight of the formulation):

a) said agrochemically active compound(s) is from 0.1%-60% by weight,
b) said solvent is from 5%-80% by weight,
c) said emulsifier is from 0.5%-80% by weight,
d) said polyethylene glycol (average molecular weights ranging from 200 to 400) and/or polypropylene glycol (average molecular weights ranging from 200 to 400) or mixtures is from 10%-90% by weight;
e) said optional dispersant is from 0-10% by weight;
f) one or more additional optional agrochemically acceptable additives can be present in an amount up to that sufficient to sum to 100%.

DETAILED DESCRIPTION OF SPECIFIC EMBODIMENTS

The individual agrochemically active ingredients, and many or all of the other components of the formulation to be used for a formulation of crop protection agents are generally known to the person skilled in the art and commercially available.

Suitable agrochemically active compounds are preferably substances having insecticidal, acaricidal, nematocidal, and/or fungicidal properties.

Suitable insecticides include Abamectin, Spinosad, Spinetoram, Imidacloprid, Chlorpyrifos, Oxyfluorfen, clothianidin, thiacloprid, thiamethoxam, nitenpyram, acetamiprid, dinotefuran, lufenuron, bifenthrin, cyperimethrin, deltamethrin, permethrin, natural pyrethrum, fenpropathrin, cyfluthrin, β-cyfluthrin, methiocarb, thiodicarb, aldicarb and, the group of the ketoenol derivatives maybe mentioned, by way of example.

Suitable fungicides include active compounds from the group of the azoles, the strobilurin derivatives, and the amino acid derivatives. Tebuconazole, prothioconazole, cyproconazole, triticonazole, triadimenol, myclobutanil, fluoxastrobin, fluquinconazole, trifloxystrobin, azoxystrobin, kresoxim-methyl, pyraclostrobin, carpropamid and iprovalicarb may be mentioned by way of example.

The formulation described herein is particularly suitable for formulating insecticidally active compounds. In particular, the formulation described herein is especially suitable for formulating active compounds from the class of the macrolides, such as, for example, the active compounds Abamectin, Spinosad, and Spinetoram. In the same preferred manner, the formulations according to the abovementioned active compounds Abamectin, Spinosad, or Spinetoram may be combined with additional agrochemically active compounds, such as, for example, additional insecticides, fungicides, plant compatibility-improving active compounds (safeners) or plant growth-promoting substances, etc.

The formulations described herein are especially well suited for formulating the agrochemically active compound Abamectin. Abamectin is emphasized as a particularly preferred active compound which can be formulated in a particularly advantageous manner with the formulation as described herein, optionally in combination with additional agrochemically active compounds, desirably additional crop protection agents.

Suitable emulsifiers include nonionic, anionic, or cationic compounds with surfactant properties which are customarily employed in agrochemical compositions. These compounds include, as examples, reaction products of fatty acids, fatty esters, fatty alcohols, fatty amines, alkylphenols or alkylarylphenols with ethylene oxide and/or propylene oxide and/or butylene oxide, and also their sulphuric esters, phosphoric monoesters and phosphoric diesters, furthermore reaction products of fatty acids, fatty esters, fatty alcohols, fatty amines, alkylphenols or alkylarylphenols with the reaction product of ethylene oxide with propylene and also alkylsulphonates, alkyl sulphates, aryl sulphates, tetraalkylammonium halides, trialkylarylammonium halides and alkylaminesulphonates. The emulsifiers can be employed individually or as mixtures with each other or with other additives, including other emulsifiers. Reaction products of castor oil with ethylene oxide in a molar ratio of from 1:20 to 1:60, reaction products of $C_6$-$C_{20}$-alcohols with ethylene oxide in a molar ratio of from 1:5 to 1:50, reaction products of fatty amines with ethylene oxide in a molar ratio of from 1:2 to 1:25, reaction products of 1 mol of phenol with 2 to 3 mol of styrene and 10 to 50 mol of ethylene oxide, reaction products of $C_8$-$C_{12}$-alkylphenols with ethylene oxide in a molar ratio of from 1:5 to 1:30, alkylglycosides, salts of $C_8$-$C_{16}$ alkylbenzenesulphonic acid, such as, for example, calcium, monoethanolammonium, diethanolammonium and triethanolammonium salts, may be mentioned as being preferred examples.

Examples of suitable nonionic emulsifiers which may be mentioned are the products known under the names Sapogenat T180 (tri-sec-butylphenol ethoxylate, from Clariant), Alkamuls OR36 (castor oil ethoxylate, from Rhodia) and Emulsogen TS54 (tristyrylphenol ethoxylate, Clariant). Preferred for use in the formulations described herein are the tristyrylphenol ethoxylates (Emulsogen TS54).

Examples of suitable anionic emulsifiers which may be mentioned are the Bayer AG product which is commercially available under the name Baykanol SL (condensate of sulphonated ditolyl ether with formaldehyde), and also phosphated or sulphated tristyrylphenol ethoxylates, where specific mention may be made of Soprophor FLK and Soprophor 4D 384 (from Rhodia).

Suitable dispersants which may be present in the crop treatment compositions disclosed herein include compounds customarily used for such purposes in agrochemical compositions. In the formulations described herein, preference is given to using copolymers of polyvinylpyrrolidone and polyvinyl acetate, which are generally present in a ratio of from 60 to 40. An example of such a copolymer is Luvitec VA 64 (BASF) which is commercially available. Vinylpyrrolidone/vinyl acetate copolymers 60:40 are particularly suitable for preparing the formulations according to the invention.

Examples of solvents which may be present in the crop treatment compositions described herein include compounds which are customarily used for such purposes in agrochemical compositions. Dimethyl sulphoxide or N-methylpyrrolidone for example, have extremely good solvent properties and are frequently used for preparing EC or EW formulations, and are also preferred for the formulations described herein.

Polyethylene glycol (average molecular weights ranging from 200 to 400) and polypropylene glycol (average molecular weights ranging from 200 to 400) are, under most conditions, stable and non-corrosive. As solvents, polyethylene glycol (average molecular weights ranging from 200 to 400) and/or polypropylene glycol (average molecular weights ranging from 200 to 400) are used in a variety of different items, such as, for example, in inks, dyes, products for removing coatings and paints, all-purpose cleaners, in products for removing fat, in cleaners for metal and machinery, and in tar removers, for example.

In the context of the present disclosure it was surprisingly found that polyethylene glycol (average molecular weights ranging from 200 to 400) and/or polypropylene glycol (average molecular weights ranging from 200 to 400) is not only suitable as an adequate substitute for VOCs in agrochemical formulations but, surprisingly, also improves foliar penetration of an agrochemically active compound when formulated as described herein. This effect is notable with the agrochemically active formulation alone and also in tank mixes with additives customary for such mixtures.

In the present disclosure, for the first time, it is shown that polyethylene glycol (average molecular weights ranging from 200 to 400) and/or polypropylene glycol (average molecular weights ranging from 200 to 400) can be used as a basis for formulation of crop protection agents, which formulations have unexpectedly excellent activity and are surprisingly easy to use.

Examples of suitable polyethylene glycols (average molecular weights ranging from 200 to 400) are selected from Polyglykol 200 (from Clariant), Polyglykol 300 (from Clariant), Polyglykol 400 (from Clariant).

Examples of suitable polypropylene glycols (average molecular weights ranging from 200 to 400) are selected from PPG 200 (Haishihua), PPG 300 (Haishihua), or PPG 400 (Haishihua).

Examples of suitable additional additives which may be present in the formulations according to the invention include crystallization inhibitors, wetting agents, and water.

Examples of suitable crystallization inhibitors which may be present in the crop treatment compositions according to the invention include any compounds customarily used for such purposes in agrochemical compositions. Copolymers of polyvinylpyrrolidone and polyvinyl alcohol, such as, for example, the polyvinylpyrrolidone/polyvinyl alcohol copolymer known under the name Luvitec VA 64 (from BASF), as well as dimethyl alkylcarboxamides, such as dimethyl decanecarboxamide, or the dimethyl $C_{6-12}$-alkanecarboxamide mixtures known under the name Hallcomid® (from Hall Comp.) maybe mentioned as being particularly suitable, as well as copolymers of ethylene diamine with ethylene oxide and propylene oxide, such as, for example, the product known under the name Synperonic T304 (from Uniqema).

Examples of suitable wetting agents include any compounds customarily used for such purposes in crop treatment compositions. Alkylphenol ethoxylates, dialkyl sulphosuccinates (such as dioctyl sulphosuccinate sodium), lauryl ether sulphates, and polyoxyethylene sorbitan fatty esters may be mentioned as being particularly suitable.

The agrochemically active formulations, and their precursor formulations, as described herein are generally prepared by mixing the liquid components of the formulation in any order with stirring at room temperature. Solid components may be dissolved in the resulting mixture.

In a particular preparation process, the agrochemically active formulations described herein are prepared by:
  a) dissolving the active compound or the active compounds in the solvent or in the solvent/cosolvent mixture,
  b) adding the emulsifier and the dispersant with stirring, and
  c) stirring the components until a clear homogeneous solution has been formed.

Suitable for preparing the crop treatment compositions described herein are customary apparatuses used for preparing agrochemical formulations.

The application rate of the crop treatment compositions according to the invention can be varied within a relatively wide range. The application rate used may depend on the particular agrochemically active compounds present in each case, and on their concentration in the crop treatment composition.

It has been found that the agrochemically active formulations as described herein are highly suitable for applying the agrochemically active compounds contained therein to plants, including seedlings, leaves, flowers, and stems/trunk as well as for applying the agrochemically active compounds to the habitat of plants, e.g., the soil in which the plants grow, as well as to soil-free substrates.

The agrochemically active formulations described herein are distinguished in particular by the fact that, by using polyethylene glycol (average molecular weights ranging from 200 to 400) or polypropylene glycol (average molecular weights ranging from 200 to 400), the biological efficacy of an agrochemically active compound in the formulation is increased considerably.

As the agrochemically active compound, the formulations described herein in particular desirably comprise an insecticide from the class of the macrolides, especially preferably Abamectin. In addition, the formulations desirably also include polyethylene glycol (average molecular weights ranging from 200 to 400) and/or polypropylene glycol (average molecular weights ranging from 200 to 400), more particularly, Polyglykol 300, Polyglykol 400, PPG-200, and/or PPG-400 as well as the additives mentioned above. Preferred polyethylene glycols include Polyglykol 300 and Polyglykol 300. Preferred polypropylene glycols include PPG-200 and PPG-400.

The agrochemically active formulations and crop treatment compositions disclosed herein can desirably be used in a particularly advantageous manner for treating cotton, citrus fruit, tomatoes, cucumbers, courgettes, aubergines, melons, cabbage species, potatoes, oilseed rape, pome fruit, stone fruit, soft fruit, grapevines, tobacco, maize, soybeans, sugarcane, ornamental plants, as well as wheat, barley, rye, oats, triticale, rice, peas, broad beans, cotton, sunflowers and beet. The formulations can also be used to treat other vegetables of different types. These include, inter alia, artichokes, cauliflower, broccoli, green beans, fennel, endive, kohlrabi, head lettuce, cress, leek vegetables, swiss chard, carrots, bell peppers, rhubarb, beetroot, red cabbage, brussels sprouts, celeriac, savoy cabbage, chestnuts, runner beans, scorzonera, asparagus, cablebeet, spinach, white cabbage, onions, and courgettes.

The agrochemically active formulations described herein, and the crop treatment compositions preparable therefrom by further mixing with formulation auxiliaries and/or crop treatment agents, are highly suitable for applying agrochemically active compounds to plants and/or plant habitat. The formulations and compositions ensure that the active components are released over a relatively long period of time in the amount desired in each case. Accordingly, another embodiment disclosed herein relates to methods for protecting plants against pests by treating the plants and/or their habitat with an agrochemically active formulation or crop treatment composition as disclosed herein.

Examples of the abovementioned pests include:
From the order of the Isopoda, for example, *Oniscus asellus, Armadillidium vulgare*, and *Porcellio scaber*.

From the order of the Diplopoda, for example, *Blaniulus guttulatus*.

From the order of the Chilopoda, for example, *Geophilus, carpophagus*, and *Scutigera* spp.

From the order of the Symphyla, for example, *Sculigerella immaculata*.

From the order of the Thysanura, for example, *Lepisma saccharina*.

From the order of the Collembola, for example, *Onychiurus armatus*.

From the order of the Orthoptera, for example, *Acheta domeslicus, Gryllotalpa* spp, *Locusta migraloria* migratorioides, *Melanoplus* spp., *Schistocerca gregaria*.

From the order of the *Blattaria*, for example, *Blatta orientalis, Periplaneta americana, Leucophaea maderae*, and *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus* corporis, *Haematopinus* spp., *Linognalhus* spp., *Trichodecles* spp., and *Damalinia* spp.

From the order of the Thysanoptera, for example, *Hercinothrips femoralis, Thripstabaci, Thrips palmi,* and *Frankliniella occidentalis.*

From the order of the Heteroptera, for example, *Eurygaster* spp., *Dysdercus intermedius, Piesma quadrata, Cimex lectularius, Rhodnius prolixus,* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphisfabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., and *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnis tis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Alomaria* spp., *Oryzaephilus Surinamensis, Anthonomus* spp., *Sitophilus* spp., *Otiorrhynchus sulcatus, Cosmopolites sordidus, Ceuthorrhynchus assimilis, Hyperapostica, Dermestes* spp., *T. rogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molilor, Agrioles* spp., *Conoderus* spp., *Melolontha melolontha, Amphimallon solstitialis, Costelytra Zealandica,* and *Lissorhoptrus oryzophilus.*

From the order of the Hymenoptera, for example, *Diprion* spp., *Hoplocampa* spp., *Lasius* spp., *Monomorium pharaonis,* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Culerebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., and *Liriomyza* spp.

From the order of the Siphonaptera, for example, *Xenopsylla cheopis,* and *Cerato phyllus* spp.

From the class of the arachnids, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus similis, Ditylenchus dipsaci, Tylenchulus semipenetrans, Helerodera* spp., *Globodera* spp., *Meloidogyne* spp., *Aphelenchoides* spp., *Longidorus* spp., *Xiphinema* spp., *Trichodorus* spp., *Bursaphelenchus* spp.

The agrochemically active formulations and crop treatment compositions described herein can be applied to or introduced into the soil or alternative cultivation substrates, such as, for example, peat, standard soil, mineral wool, nutrient solutions, irrigation water, etc., to the plants (for example foliar application) or parts of plants (for example stem application) or else to the seed of the plants mentioned above for the corresponding propagation material.

In general, when treating plants, the amount of the formulation or composition described herein, and/or further additives that are applied, has to be chosen such that the plant is not damaged. This is especially important in the case of agrochemically active compounds which, at certain application rates, may show phytotoxic effects.

The application rate of the formulations as described herein and the preparations preparable therefrom by further mixing with formulation auxiliaries (e.g., crop treatment compositions) can be varied within a relatively wide range. When treating parts of plants, the application rates of the active compound are generally between 0.1 and 10000 g/ha, more particularly between 10 and 1000 g/ha.

The preparation and the use of the formulations according to the invention is illustrated by the examples below, which are not intended to limit the scope of the invention.

EXAMPLES

Example 1

Preparation of a Formulation Based on Abamectin and Polyglykol 300 (from Clariant)

The liquid components listed in Table 1 below are, in any order, mixed with stirring at room temperature until a homogeneous liquid is obtained. Solid components are dissolved in the resulting mixture. Amounts of components are given in weight percent, based on the weight of the resulting formulation, unless otherwise indicated.

This gives a formulation with the following composition:

TABLE 1

| Ingredients | Weight % | Function |
| --- | --- | --- |
| Abamectin | 1.8 | Active compound |
| Tristyrylphenol 54M ethoxylate( Emulsogen TS54) | 2.5 | Emulsifier |
| VP/VA copolymer ( Luvitec VA 64 from BASF) | 1 | Dispersant |
| Polyglykol 300 (from Clariant) | 89.7 | Cosolvent |
| N-methylpyrrolidone (NMP) | 5 | Solvent |

Comparative Example 1

The liquid components listed in Table 2 below are, in any order, mixed with stirring at room temperature until a homogeneous liquid is obtained. Solid components are dissolved in the resulting mixture.

TABLE 2

| Ingredients | Weights % | Function |
|---|---|---|
| Abamectin | 1.8 | Active compound |
| Tristyrylphenol 54M ethoxylate (Emulsogen TS54) | 2.5 | Emulsifier |
| VP/VA copolymer (Luvitec VA 64 from BASF) | 1 | Disperstant |
| N-methylpyrrolidone (NMP) | 94.7 | Solvent |

Example 2

Determination of the Bioavailability (Penetration of the Cuticles) of the Formulated Active Compound in Example 1 (Contain Polyglykol 300) and Comparative Example 1.

The formulations of Example 1 and Comparative Example 1 were compared with respect to the penetration of the cuticles of apple leaves (cultivar Golden Delicious) by the composition (Table 3).

Fully developed leaves were cut from the apple trees, and the cuticles were isolated by the following procedure:

initial filling of leaf discs, the underside of which had been marked with dye and which had been punched out, was by vacuum infiltration with a pectase solution (0.2 to 2%) buffered to a pH between 3 and 4;

sodium azide was then added to the leaf discs; and the treated leaf discs were allowed to stand until the original leaf structure had been dissolved and the non-cellular cuticles had been detached;

cuticles free from stomata and hairs from the upper sides of the leaves were selected for testing;

the selected cuticles were repeatedly washed, alternating with water and a buffer solution at pH 7.

The resulting clean cuticles were then mounted on Teflon plates and straightened and dried using a gentle stream of air.

In the next step, the cuticle membranes obtained in this manner were, for membrane transport studies, placed into diffusion cells (transport chambers) made from stainless steel. To this end, the cuticles were, using a pair of tweezers, placed into the middle of the edges of the diffusion cells, which had been coated with silicone grease, and the cuticles were closed using a ring which had also been treated with grease. The arrangement was chosen such that the morphological outside of the cuticles was facing out, i.e., to the atmosphere, whereas the morphological inside of the cuticles was facing toward the inside of the diffusion cell. The diffusion cells were filled with water or a water/solvent mixture, and the membranes then sprayed with the spray liquors. For the spray liquors, the formulations of Example 1 and of Comparative Example 1 were diluted with CIPAC water before spraying.

After the spray liquors had been applied, the water was in each case allowed to evaporate, and the chambers were then in each case turned over and placed into thermostatically controlled tubs. The penetration was evaluated at a relative atmospheric humidity of 60% and a temperature adjusted to 20° C. Using a syringe, samples were taken at regular intervals and, using HPLC, examined for the content of penetrated active compound.

The test results are shown in Table 3 below.

TABLE 3

| Formulation | Abamectin concentration (g/L) | Penetration after 1 day$^{a*}$ (±SE) | Penetration after 2 days$^{a*}$ (±SE) | Penetration after 5 days (±SE)$^{a**}$ |
|---|---|---|---|---|
| Example 1 | 0.1 | 5.4% (±0.5) | 9.7% (±0.8) | 16.5% (±1.0) |
| Comparative Example 1 | 0.1 | 2.2% (±0.8) | 5.3% (±1.0) | 10.2% (±1.0) |

$^a$An average of 18-20 repetitions was done to evaluate the penetration of the agrochemically active compound through apple leaf cuticles;
*Evaluation of penetration at 20° C., 60% atmospheric humidity;
**After 96 hours, temperature was increased to 30° C. (at 60% atmospheric humidity)

Example 3

Effect of a Formulation According to the Invention Based on Abamectin and Polyglykol 300

*Myzus persicae* Test

To prepare a solution suitable for application, 1 part by weight of each formulated product prepared in Example 1 and Comparative Example 1 are mixed with water to give the desired concentration.

Discs of Chinese cabbage leaves (*Brassica pekinensis*) infested by all stages of the green peach aphid (*Myzus persicae*) are sprayed with an application solution of the desired concentration.

After the desired period of time, the effect in % is determined by counting the number of aphids killed as a percentage of the total number of aphids in a sample. 100% means that all aphids have been killed; 0% means that none of the aphids have been killed.

In this test, for example, the following formulation of the Example 1 exhibits an efficacy superior to that of Comparative example 1, as shown below in Table 4.

TABLE 4

| Active compound/product | Concentration in ppm | Kill in % after 14 days |
|---|---|---|
| Example 1 | 7.2 | 98.3 |
| Comparative Example 1 | 7.2 | 85.6 |

Example 4

Effect of a Formulation According to the Invention Based on Abamectin and Polyglykol 300

*Plutella xylostella* Test (Normally Sensitive, i.e. Non-Resistant to Abamectin)

To prepare a solution suitable for application, formulated product from each of Example 1 and Comparative Example 1 is mixed with water to give the desired concentration.

Discs of Chinese cabbage leaves (*Brassica pekinensis*) are sprayed with an application solution of the desired concentration and, after the spray coating has dried on, the disc is populated with larvae of the diamond back moth (*Plutella xylostella*).

After the desired period of time, the effect in % is determined by counting the number of larvae killed as a percentage of the total number of larvae in a sample. 100% means that all larvae have been killed; 0% means that none of the larvae have been killed.

In this test, for example, the following formulation of Example 1 exhibits an efficacy superior to that of Comparative Example 1):

TABLE 5

| Active compound/product | Concentration in ppm | Kill in % after $7^d$ |
|---|---|---|
| Example 1 | 6 | 55 |
| Comparative Example 1 | 6 | 94 |

Example 5

Effect of a Formulation According to the Invention Based on Abamectin and Polyglykol 300
Plant Compatibility—Cotton To prepare a solution suitable for application, formulated product is mixed with water to give the desired concentration. Cotton plants are sprayed to run off point with an application solution of the desired concentration.

After the desired period of time, the damage to the plant is determined in %. 100% means that the entire plant has been damaged; 0% means that no damage is visible. In this test, for example, the following formulation of the example according to the invention exhibits an efficacy superior to that of the prior art (comparative example 1):

TABLE 6

| Active compound/product | Concentration in ppm | Damage in % after $7^d$ |
|---|---|---|
| Example 1 | 1000 | 0 |
| Comparative example 1 | 1000 | 15 |

Example 6

Effect of a Formulation According to the Invention Based on Abamectin and Polyglykol 300

Estimation of Volatile Emission Potential: The potential for solid or liquid pesticide to emit volatile organic compounds (VOCs) is estimated by thermogravimetric analysis (TGA). Pesticide samples are heated in an environmentally controlled chamber and then held isothermally until the rate of sample mass loss drops below a defined threshold.

TABLE 7

| Active compound/product | Method | Result Wt. % Loss |
|---|---|---|
| Example 1 | CA DPR 115C | 27.26 |
| Comparative example 1 | CA DPR 115C | 53.26 |

The invention having been described with reference to certain specific embodiments and examples, it will be understood that these specific embodiments and examples are provided to illustrate, not limit, the scope of the appended claims.

The invention claimed is:

1. An agrochemically active formulation for the treatment of a crop or crop habitat, consisting of:
   a) an agrochemically active compound, wherein said agrochemically active compound is selected from the group consisting of Abamectin, Spinosad, Spinetoram, Imidacloprid, Chlorpyrifos, Oxyfluorfen, and mixtures thereof,
   b) a solvent that completely or partially dissolves the agrochemically active compound, wherein the solvent consists of N-methylpyrrolidone, dimethyl sulphoxide, or a mixture thereof,
   c) an emulsifier,
   d) a polyethylene glycol having an average molecular weight ranging from 200 to 400, or a polypropylene glycol having an average molecular weight ranging from 200 to 400, or mixtures thereof present in an amount ranging from 10% to 90% by weight, based on the weight of the formulation,
   e) optionally, a dispersant present in an amount of 10% by weight or less based on the weight of the formulation, and
   f) optionally, a nonsolvent agrochemically acceptable additive, wherein said agrochemically active formulation exhibits insecticidal activity on crops or crop habitat when applied at a level of from 0.1 to 10000 g/ha of said argochemically active compound.

2. The agrochemically active formulation according to claim 1, wherein
   a) said agrochemically active compound is present in an amount ranging from 0.1% to 60% by weight, based on the weight of the formulation,
   b) said solvent is present in an amount ranging from 5% to 80% by weight, based on the weight of the formulation,
   c) said emulsifier is present in an amount ranging from 0.5% to 80% by weight, based on the weight of the formulation,
   d) said polyethylene glycol having an average molecular weight ranging from 200 to 400, or said polypropylene glycol having an average molecular weight ranging from 200 to 400, or mixtures thereof, is present in an amount ranging from 15% to 60% by weight, based on the weight of the formulation, and
   e) said optional dispersant is present in a positive amount ranging from greater than 0 to 10% by weight, based on the weight of the formulation.

3. The agrochemically active formulation according to claim 1, wherein the polyethylene glycol has an average molecular weights of 200, 300, or 400.

4. The agrochemically active formulation according to claim 1, wherein the polypropylene glycol has an average molecular weights of 200, 300, or 400.

5. A crop treatment composition consisting of:
   an effective amount of the agrochemically active formulation according to claim 1, further diluted with water.

6. A process for preparing the agrochemically active formulation according to claim 1, comprising:
   a) dissolving the agrochemically active compound in a mixture of one or more of the solvent, and of a polyethylene glycol having an average molecular weight ranging from 200 to 400 or of a polypropylene glycol having an average molecular weight ranging from 200 to 400, or mixtures thereof;
   b) adding one or more emulsifiers and optionally one or more dispersants and optionally one or more agrochemically acceptable additives with stirring, and
   c) homogenizing the mixture obtained from (b) to form a clear and homogeneous solution.

7. A method for treating plants or protecting plants against pests, comprising contacting said plants or their habitat with the crop treatment composition according to claim 5.

8. A method for increasing the efficacy of an active compound or a combination of active compounds, comprising formulating said active compound or combination of active compounds in an agrochemically active formulation according to claim 1.

9. A method for reducing the potential for emission of volatile organic compounds by an agrochemically active compound formulation, comprising formulating an agrochemically active compound or combination of agrochemically active compounds in an agrochemically active formulation according to claim 1.

10. The argochemically active formulation according to claim 1, wherein said dispersant is present in a positive amount of up to 10% by weight based on the total formulation weight and wherein said dispersant consists of a copolymer of polyvinylpyrrolidone and polyvinyl acetate in a ratio of 60:40.

* * * * *